United States Patent
Woo

(10) Patent No.: US 10,500,243 B2
(45) Date of Patent: Dec. 10, 2019

(54) COMPOSITION FOR COOLING SKIN COMPRISING PHELLODENDRON BARK EXTRACT, METHOD OF PREPARING THE SAME, TOPICAL COMPOSITION COMPRISING THE SAME AND DERMATOLOGICALLY ACCEPTABLE CARRIER, AND METHOD OF COOLING SKIN BY APPLYING THE SAME

(71) Applicants: Yong Kyu Woo, Suseong-gu (KR); NATURE4 CO., LTD, Gyeongsan-si, Gyeongsangbuk-do (KR)

(72) Inventor: Yong Kyu Woo, Suseong-gu (KR)

(73) Assignees: Yong Kyu Woo, Daegu (KR); NATURE FOUR CO., LTD, Gyeongsan-si (KR)

(*) Notice: Subject to any disclaimer, the term of this patent is extended or adjusted under 35 U.S.C. 154(b) by 0 days.

(21) Appl. No.: 16/237,456

(22) Filed: Dec. 31, 2018

(65) Prior Publication Data
US 2019/0134135 A1    May 9, 2019

Related U.S. Application Data

(60) Division of application No. 15/443,675, filed on Feb. 27, 2017, now Pat. No. 10,201,581, which is a (Continued)

(30) Foreign Application Priority Data

Aug. 27, 2014   (KR) .................. 10-2014-0112062

(51) Int. Cl.
*A61K 36/756*    (2006.01)
*A61K 36/75*    (2006.01)
(Continued)

(52) U.S. Cl.
CPC .......... *A61K 36/756* (2013.01); *A61K 9/0014* (2013.01); *A61K 33/06* (2013.01);
(Continued)

(58) Field of Classification Search
None
See application file for complete search history.

(56) References Cited

U.S. PATENT DOCUMENTS

2009/0130231 A1   5/2009   Chen
2009/0253666 A1   10/2009   Lintner et al.

FOREIGN PATENT DOCUMENTS

JP    2003012445 A    1/2003
KR    2011116964 A    12/2001
(Continued)

OTHER PUBLICATIONS

You et al. (Ultrasound-assisted Vacuum Extraction of Polyphenols from Jujube Peel, Chemistry and Industry of Forest, 2014, vol. 34, No. 1, pp. 107-112. (Year: 2014).*

(Continued)

*Primary Examiner* — Robert A Wax
*Assistant Examiner* — Melissa S Mercier
(74) *Attorney, Agent, or Firm* — Sughrue Mion, PLLC

(57) ABSTRACT

Provided are a composition for cooling skin comprising a Phellodendron bark extract, a method of preparing the composition, a skin-improving product comprising the composition and a method of cooling skin by applying the composition to a skin of a subject, wherein the skin needs cooling. The composition prevents a burning sensation in the skin and under the skin and reduces heat generated under the skin and on the skin. The composition includes a Phellodendron bark extract as a main ingredient and further includes an extract of one or more selected from the group consisting of *Anemarrhena asphodeloides, Scutellaria*
(Continued)

*baicalensis, Paeonia lactiflora, Dictamnus dasycarpus, Alumen, Dryobalanops aromatic* and *Mentha arvensis*.

6 Claims, 8 Drawing Sheets

Related U.S. Application Data continuation-in-part of application No. PCT/KR2015/005077, filed on May 21, 2015.

(51) Int. Cl.
    *A61K 36/8964*      (2006.01)
    *A61K 9/00*      (2006.01)
    *A61K 33/06*      (2006.01)
    *A61K 36/18*      (2006.01)
    *A61K 36/534*      (2006.01)
    *A61K 36/539*      (2006.01)
    *A61K 36/65*      (2006.01)

(52) U.S. Cl.
    CPC ............ *A61K 36/18* (2013.01); *A61K 36/534* (2013.01); *A61K 36/539* (2013.01); *A61K 36/65* (2013.01); *A61K 36/75* (2013.01); *A61K 36/8964* (2013.01); *A61K 2236/13* (2013.01); *A61K 2236/331* (2013.01)

(56) References Cited

FOREIGN PATENT DOCUMENTS

| | | |
|---|---|---|
| KR | 10-2008-0097685 A | 11/2008 |
| KR | 10-2011-0017687 A | 2/2011 |
| KR | 10-1135172 B1 | 4/2012 |
| KR | 10-2014-0020144 A | 2/2014 |
| KR | 10-2014-0032516 A | 3/2014 |

OTHER PUBLICATIONS

Wu et al. (Constituents from the Leaves of *Phellodendron amurense* var. *wilsonii* and Their Bioactivity. J. Nat. Prod. 2003, 66, 9, 1207-1211. (Year: 2003).*
International Searching Authority, International Search Report for PCT/KR2015/005077 dated Sep. 9, 2015.
Korean Intellectual Property Office, Office Action dated Nov. 25, 2015 issued in counterpart KR application No. 10-2014-0112062.
Chul-Hee Hong, "Two cases of Seborrheic Dermatitis treated by Hwangryunhaedok-tang Pharmacopuncture Therapy", The Journal of Korean Oriental Medical Ophthalmology & Otolaryngology & Dermatology, 2012, pp. 68-75, vol. 25, No. 2.
In-Soon Bae et al., "Application Tests of Phellodendrin cortex Water Extract As Functional Cosmetic Raw Materials", Journal of Investigative Cosmetology, 2012, pp. 1-8, vol. 8, No. 1.
Phellodendron Bark (The Tillotson Institute of Natural Health, available online Feb. 22, 2006) (Year: 2006).
Herbal Combination List, available online Sep. 25, 2000 (Year: 2000).
Single Herbs (Chinese Herbal Medicine, available online Nov. 4, 2013) (Year: 2013).
Preservatives in Cosmetics-Natural vs Synthetic, published Jun. 9, 2010 (Year: 2010).

* cited by examiner

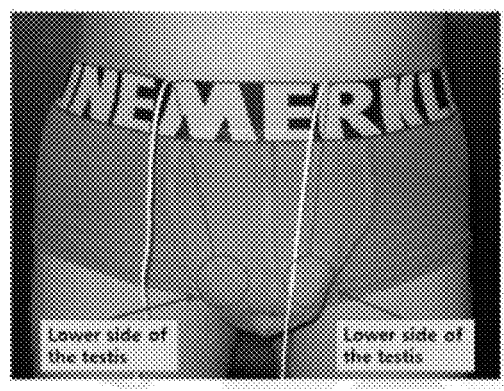 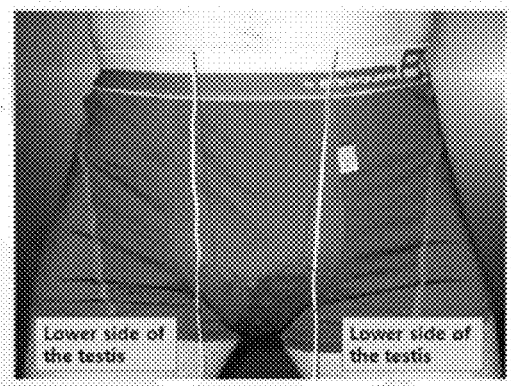
Test Person A　　　　Test Person B

COMPOSITION FOR COOLING SKIN COMPRISING PHELLODENDRON BARK EXTRACT, METHOD OF PREPARING THE SAME, TOPICAL COMPOSITION COMPRISING THE SAME AND DERMATOLOGICALLY ACCEPTABLE CARRIER, AND METHOD OF COOLING SKIN BY APPLYING THE SAME

CROSS-REFERENCE TO RELATED APPLICATIONS

This application is a Rule 53(b) Divisional of U.S. application Ser. No. 15/443,675 filed Feb. 27, 2017, which is a bypass continuation-in-part of International Application No. PCT/KR2015/005077 filed May 21, 2015, which claims benefit of Korean Patent Application No. 10-2014-0112062 filed Aug. 27, 2014, the entire contents of which are incorporated by reference in their entirety.

TECHNICAL FIELD

The present disclosure relates to a composition for cooling skin comprising a Phellodendron bark extract, a method of preparing the composition, a topical composition comprising the composition and a dermatologically acceptable carrier, and a method of cooling skin by applying the composition to a skin of a subject, wherein the skin needs cooling. The composition prevents a burning sensation in the skin and under the skin and reduces heat generated under the skin and on the skin. The composition not only cools the skin where the composition is applied, but also maintains the temperature of the skin at a normal range.

BACKGROUND ART

Generally, when fever occurs in a specific area of a human body, in particular, in the case of occurrence of high fever, many different skin problems such as skin itching, eczema as well as headache, diarrhea, and chills occur, which may be temporarily alleviated or mitigated by, for example, medications. However, when fever occurs in newborn babies, infants, or pregnant women, etc., for which drug administration or drug intake is sometimes restricted, it may be difficult to take an immediate action to timely and properly reduce the fever, which leads to an emergency situation.

It is well known that the temperature of man's testis is required to be maintained about 2° C. lower than the body temperature in order to produce and store sperms and to produce male hormones. When the testicular temperature is 1° C. higher than the normal reference temperature, sperm counts and mobility decrease by about 40%. When the testicular temperature is 2° C. higher than the normal reference temperature, or when a temperature increase occurs frequently, the testicles lose their functions, which cause infertility, sterility, or decline in the sexual function as well as a rapid increase in the incidence of testicular cancer.

Sitting for 2 hours or wearing tight or heavy clothing that insulates the scrotal area can raise scrotal temperature by about 1-2° C. For baby boys, wearing disposable diapers, urine, and feces over the period of time may have serious adverse effects on the testicles of baby boys, and lead to many side effects such as rash, maceration, etc.

In the modern society, there are many factors that raise men's testicular temperature, such as wearing of tight pants with poor ventilation, working, studying, driving, travelling for long distances, or leisure activities such as riding a bicycle or motorcycle. The severity thereof is well known, and therefore, functional men's underwear to separate the penis from the scrotum has been developed and sold. However, it is difficult to avoid the increase of the testicular temperature because of the sitting posture. In particular, there are no appropriate alternatives to disposable diapers for baby boys.

To solve these problems, the present disclosure discloses a technology of using a Phellodendron bark as an effective ingredient to prevent a burning sensation in the skin and under the skin and to reduce heat generated under the skin and on the skin, and also to provide prophylactic and therapeutic effects in the case of itching, eczema, odor, furuncle, or rash.

As an example of previously known compositions including Phellodendron bark, Korean Patent Publication No. 10-2011-0017687 discloses a composition for inhibiting acne-caused hyperpigmentation. However, in this patent, there is no disclosure regarding the effects of preventing a burning sensation in the skin and under the skin and of reducing heat generated under the skin and on the skin. This patent intends to simply provide a composition for external use such as cosmetics by using the Phellodendron bark extract.

Further, as another example, Korean Patent No. 10-1135172 discloses a pharmaceutical composition for preventing, improving, or treating acne, including an extract mixture of Phellodendron bark, Houttuynia cordata, *Paeonia lactiflora* Pall, Agrimonia pilosa Ledeb, and *Glycyrrhiza uralensis* Fisch as an active ingredient. However, in this patent, there is no disclosure regarding the effects of preventing a burning sensation in the skin and under the skin and of reducing the generated heat under the skin and on the skin.

Accordingly, the present disclosure aims to develop a composition for preventing a burning sensation in the skin and under the skin and reducing heat generated under the skin and on the skin by using a composition including a Phellodendron bark extract, a method of preparing the same, and a skin-improving product using the same.

DETAILED DESCRIPTION OF THE INVENTION

In order to solve the above-described problems, an object of the present disclosure is to provide a composition for cooling skin comprising a Phellodendron bark extract to prevent a burning sensation in the skin and under the skin and to reduce heat generated under the skin and on the skin.

The composition also exhibits prophylactic and therapeutic effects on itching, eczema, odor, furuncle, or rash.

The composition can be used to prepare skin-cooling and skin-improving products such as a functional spray, an ointment, a gel, a cream, a powder, a patch pad, etc.

In order to achieve the above objects, the present disclosure provides a composition for cooling skin comprising a Phellodendron bark extract as a main ingredient.

The term "main ingredient" as used herein, refers to an ingredient which by itself may impart an effect of cooling skin.

In the embodiments, various parts of the plants may be employed, including flower, root, bark, leaf, stem, sap, seed, berries, etc. A whole plant may be used. Mixtures of different parts of the plant can be used.

The plants may be used as a raw plant, steamed plant, air dried plant, steamed-dried plant, vacuum dried plant. In an embodiment, raw plants or dried plants are used.

The term "plant" as used herein, refers to a whole plant, a part of the plant, either in intact raw material form, or processed by way of steaming, drying, pulverizing, smashing, or the like.

The composition may further comprise an extract of *Anemarrhena asphodeloides*.

The composition may further comprise an extract of one or more selected from the group consisting of *Anemarrhena asphodeloides*, *Scutellaria baicalensis*, *Paeonia lactiflora*, *Dictamnus dasycarpus*, *Alumen*, *Dryobalanops aromatic*, *Mentha arvensis*, *Inula helenium*, *Lonicera japonica*, *Eclipta prostrata* and *Glycyrrhiza uralensis* FISCH.

The composition may further comprise an extract of *Anemarrhena asphodeloides*, *Scutellaria baicalensis*, *Paeonia lactiflora*, *Dictamnus dasycarpus*, *Alumen*, *Dryobalanops aromatic* and *Mentha arvensis*.

The composition may further comprise an extract of *Anemarrhena asphodeloides*, *Scutellaria baicalensis*, *Paeonia lactiflora*, *Dictamnus dasycarpus*, *Alumen*, *Dryobalanops aromatic*, *Mentha arvensis* *Inula helenium*, *Lonicera japonica*, *Eclipta prostrata* and *Glycyrrhiza uralensis* FISCH.

The composition can be included in a topical composition together with a dermatologically acceptable carrier.

The composition can include 0.01% to 100% by weight of an extract of (i) one or more plant(s) selected from the group consisting of Phellodendron bark, *Anemarrhena asphodeloides*, *Scutellaria baicalensis*, *Paeonia lactiflora*, *Dictamnus dasycarpus*, *Alumen*, *Dryobalanops aromatic* and *Mentha arvensis*, (ii) at least one part of the one or more plant(s), or (iii) a mixture of the one or more plant(s) and at least one parts of the one or more plant(s).

The lower limit above may be 1% by weight, 2% by weight, 3% by weight, 4% by weight, 5% by weight, 6% by weight, 7% by weight, 8% by weight, 9% by weight, 10% by weight, 20% by weight, 30% by weight, 40% by weight, 50% by weight, 60% by weight, 70% by weight, 80% by weight, 90% by weight, 91% by weight, 92% by weight, 93% by weight, 94% by weight, 95% by weight, 96% by weight, 97% by weight, 98% by weight, 98.5% by weight and 99.0% by weight.

The upper limit above may be 99.0% by weight, 98.5% by weight, 98% by weight, 97% by weight, 96% by weight, 95% by weight, 94% by weight, 93% by weight, 92% by weight, 91% by weight, 90% by weight, 80% by weight, 70% by weight, 60% by weight, 50% by weight, 40% by weight, 30% by weight, 20% by weight, 10% by weight, 9% by weight, 8% by weight, 7% by weight, 6% by weight, 5% by weight, 4% by weight, 3% by weight, 2% by weight and 1% by weight.

The composition may comprise 30-80% by weight of a Phellodendron bark extract and 20-70% by weight of an *Anemarrhena asphodeloides* extract.

In this disclosure, the weight could be any one of raw plants weight, dried plants weight and steamed plants weight.

The composition may comprise 35-50% by weight of an extract of Phellodendron bark and *Anemarrhena asphodeloides* and 50-65% by weight of an extract of *Scutellaria baicalensis*, *Paeonia lactiflora*, a *Dictamnus dasycarpus*, *Alumen*, *Dryobalanops aromatic* and *Mentha arvensis*.

The composition may comprise 15-35% by weight of a Phellodendron bark extract, 10-23% by weight of an *Anemarrhena asphodeloides* extract, 3-15% by weight of a *Scutellaria baicalensis* extract, 12-25% by weight of a *Paeonia lactiflora* extract, 7-15% by weight of a *Dictamnus dasycarpus* extract, 12-25% by weight of an *Alumen* extract, 0.7-5% by weight of a *Dryobalanops aromatic* extract and 1-7% by weight of a *Mentha arvensis* extract.

The composition may comprise 35-50% by weight of an extract of Phellodendron bark and *Anemarrhena asphodeloides* and 50-65% by weight of an extract of *Scutellaria baicalensis*, *Paeonia lactiflora*, a *Dictamnus dasycarpus*, *Alumen*, *Dryobalanops aromatic*, *Mentha arvensis*, *Inula helenium*, *Lonicera japonica*, *Eclipta prostrata* and *Glycyrrhiza uralensis* FISCH.

The composition may comprise 15-35% by weight of a Phellodendron bark extract, 10-23% by weight of an *Anemarrhena asphodeloides* extract, 3-15% by weight of a *Scutellaria baicalensis* extract, 12-25% by weight of a *Paeonia lactiflora* extract, 7-15% by weight of a *Dictamnus dasycarpus* extract, 12-25% by weight of an *Alumen* extract, 0.7-5% by weight of a *Dryobalanops aromatic* extract and 1-7% by weight of a *Mentha arvensis* extract, 1-7% by weight of an *Inula helenium* extract, 3-15% by weight of a *Lonicera japonica* extract, 7-15% by weight of an *Eclipta prostrata* extract and 3-15% by weight of a *Glycyrrhiza uralensis* FISCH extract.

The composition may comprise an extract of Phellodendron bark, *Scutellaria baicalensis*, *Paeonia lactiflora* and *Mentha arvensis*.

The composition may comprise the Phellodendron bark extract is in an amount of 15-60% by weight, the *Scutellaria baicalensis* extract is in an amount of 3-30% by weight, the *Paeonia lactiflora* extract is in an amount of 12-50% by weight and the *Mentha arvensis* extract is in an amount of 5-25% by weight.

Any composition discussed above may further comprise an extract of one or more of *Inula helenium*, *Lonicera japonica*, *Eclipta prostrata* and *Glycyrrhiza uralensis* FISCH.

Extractions of plants may be carried out by conventional methods. The extract can be an aqueous extract or a non-aqueous extract. The extract can be extracted with alcohol (e.g., methanol, ethanol propanol, butanol, etc.), glycols, oils, water, etc. The extract can be an aqueous or a non-aqueous extract. The aqueous extract can include an alcohol, a glycol, water and/or water. Non-aqueous extract can include a fat or an oil.

For instance, the extraction may be carried out as follows. 600-1,200 g of Phellodendron bark is washed with purified water, and then put in a super fast low temperature vacuum extractor which contains a liquid phase extractor and a gas phase distillation part, together with 15-25 L of a first solvent, and a vacuum extraction is performed for 50-80 minutes at 60-80° C. to obtain a distillation solution in the gas phase distillation part and a liquid extract in the liquid phase extractor, and optionally, the first solvent from the liquid extract is removed to obtain a concentrated extract. The distillation solution and/or the concentrated extract is used as a plant extract. Such a plant extract may be used in preparing a composition for cooling skin. The first solvent is one or more selected from the group consisting of alcohol, glycols, oils, water and purified water.

In the extraction above, the lower limit of the amount of the first solvent may be 15 L, 15.5 L, 16 L, 16.5 L, 17 L, 17.5 L, 18 L, 18.5 L, 19 L, 19.5 L, 20 L, 20.5 L, 21 L, 21.5 L, 22 L, 22.5 L, 23 L, 23.5 L, 24 L or 24.5 L, and the upper limit of the amount of the first solvent may be 15.5 L, 16 L, 16.5

L, 17 L, 17.5 L, 18 L, 18.5 L, 19 L, 19.5 L, 20 L, 20.5 L, 21 L, 21.5 L, 22 L, 22.5 L, 23 L, 23.5 L, 24 L, 24.5 L or 25 L.

Further, the extraction may be carried out as follows. 600-1,200 g of Phellodendron bark is washed with purified water, and then put in a super fast low temperature vacuum extractor which contains a liquid phase extractor and a gas phase distillation part, together with 15-25 L of a first solvent, and a vacuum extraction is performed for 50-80 minutes at 60-80° C. to obtain a distillation solution in the gas phase distillation part and a liquid extract in the liquid phase extractor, and optionally the first solvent is removed from the liquid extract to obtain a concentrated extract. In addition, 80-130 g of *Alumen* is added to 3-10 L of a second solvent and warm impregnation is performed at 65-80° C. for 50-80 minutes and filtered, and then a filtrate is mixed with the composition in a ratio of 5:1 to 1:1 (the distillation solution:the filtrate) to prepare a stock solution. The distillation solution, the concentrated extract and/or the stock solution is used as a plant extract. Such a plant extract may be used in preparing a composition for cooling skin. In the extraction process above, the ratio between the distillation solution and the filtrate may be 4.5:1, 4:1, 3.5:1, 3:1, 2.5:1, 2:1 or 1.5:1. The first solvent is one or more selected from the group consisting of alcohol, glycols, oils, water and purified water. The second solvent is one or more selected from the group consisting of alcohol, glycols, oils, water and purified water.

In addition, the extraction may be carried our as follows.

(a) washing a plant with water, wherein the plant is Phellodendron bark; and (b) putting the washed plant and a first solvent at a volume ratio of 1:12 to 1:42 in a super fast low temperature vacuum extractor which contains a liquid phase extractor and a gas phase distillation part, and performing a vacuum extraction for 50-80 minutes at 60-80° C. to obtain a distillation solution in the gas phase distillation part and a liquid extract in the liquid phase extractor; and (c) optionally, removing the first solvent from the liquid extract to obtain a concentrated extract, wherein the distillation solution in (b) or the concentrated extract in (c) is the plant extract. In the extraction process above, the first solvent is one or more selected from the group consisting of alcohol, glycols, oils, water and purified water. Such a plant extract may be used in preparing a composition for cooling skin.

In the extraction process above, the volume ratio between the washed plant and water may be 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40 or 1:41. The first solvent is one or more selected from the group consisting of alcohol, glycols, oils, water and purified water.

Further, the extraction above may further comprise (d) adding *Alumen* to a second solvent in a volume ratio of 1:23 to 1:334 and performing a warm impregnation at 65-80° C. for 50-80 minutes and filtering to obtain a filtrate; and (e) mixing the filtrate of (c) with the distillation solution of (b) in a volume ratio of 5:1 to 1:1 (the distillation solution of (b): the filtrate of (d)) to prepare a stock solution, wherein the stock solution is the plant extract. The second solvent is one or more selected from the group consisting of alcohol, glycols, oils, water and purified water. Such a plant extract may be used in preparing a composition for cooling skin.

In the extraction process above, the volume ratio between the washed plant and water may be 1:25, 1:30, 1:40, 1:50, 1:60, 1:70, 1:80, 1:90, 1:100, 1:110, 1:120, 1:130, 1:140, 1:150, 1:160, 1:170, 1:180, 1:190, 1:200, 1:210, 1:220, 1:230, 1:240, 1:250, 1:260, 1:270, 1:280, 1:290, 1:300, 1:310, 1:320 or 1:330. In the extraction process above, the ratio between the distillation solution and the filtrate may be 4.5:1, 4:1, 3.5:1, 3:1, 2.5:1, 2:1 or 1.5:1. The second solvent is one or more selected from the group consisting of alcohol, glycols, oils and water.

In the extraction above, the low temperature vacuum extraction may be performed during any time period between 30 minutes to 24 hours. The lower limit above may be 35 minutes, 40 minutes, 45 minutes, 50 minutes, 55 minutes, 60 minutes, 2 hours, 3 hours, 4 hours, 5 hours, 6 hours, 7 hours, 8 hours, 9 hours, 10 hours, 11, hours, 11 hours and 30 minutes, 12 hours, 13 hours, 14 hours, 15 hours, 16 hours, 17 hours, 18 hours, 19 hours, 20 hours, 21 hours, 22 hours or 23 hours. And the upper limit above may be 40 minutes, 45 minutes, 50 minutes, 55 minutes, 60 minutes, 2 hours, 3 hours, 4 hours, 5 hours, 6 hours, 7 hours, 8 hours, 9 hours, 10 hours, 11 hours, 11 hours and 30 minutes, 12 hours, 13 hours, 14 hours, 15 hours, 16 hours, 17 hours, 18 hours, 19 hours, 20 hours, 21 hours, 22 hours, 23 hours or 24 hours. In the extraction above, the low temperature vacuum extraction may be performed at any temperature between 30-100° C. The lower limit above may be 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 65° C., 70° C., 75° C., 80° C., 85° C., 90° C. or 95° C. And the upper limit may be 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 65° C., 70° C., 75° C., 80° C., 85° C., 90° C., 95° C. or 100° C.

In the extraction above, the low temperature vacuum extraction may be performed at a pressure of 30-40 cmHg. The lower limit above may be 30 cmHg, 30.5 cmHg, 31 cmHg, 31.5 cmHg, 32 cmHg, 32.5 cmHg, 33 cmHg, 33.5 cmHg, 34 cmHg, 34.5 cmHg, 35 cmHg, 35.5 cmHg, 36 cmHg, 36.5 cmHg, 37 cmHg, 37.5 cmHg, 38 cmHg, 38.5 cmHg, 39 cmHg or 39.5 cmHg. And the upper limit above may be 30.5 cmHg, 31 cmHg, 31.5 cmHg, 32 cmHg, 32.5 cmHg, 33 cmHg, 33.5 cmHg, 34 cmHg, 34.5 cmHg, 35 cmHg, 35.5 cmHg, 36 cmHg, 36.5 cmHg, 37 cmHg, 37.5 cmHg, 38 cmHg, 38.5 cmHg, 39 cmHg, 39.5 cmHg or 40 cmHg. 30.5 cmHg, 31 cmHg, 31.5 cmHg, 32 cmHg, 32.5 cmHg, 33 cmHg, 33.5 cmHg, 34 cmHg, 34.5 cmHg, 35 cmHg, 35.5 cmHg, 36 cmHg, 36.5 cmHg, 37 cmHg, 37.5 cmHg, 38 cmHg, 38.5 cmHg, 39 cmHg or 39.5 cmHg.

In the extraction process above, one or more of plant(s) selected from the group consisting of *Anemarrhena asphodeloides, Scutellaria baicalensis, Paeonia lactiflora, Dictamnus dasycarpus, Alumen, Dryobalanops aromatic* and *Mentha arvensis* may be used as the starting material together with Phellodendron bark (making the sum of them to be 600-1,200 g).

In the extraction process above, all of *Anemarrhena asphodeloides, Scutellaria baicalensis, Paeonia lactiflora, Dictamnus dasycarpus, Alumen, Dryobalanops aromatic* and *Mentha arvensis* may be used as the starting material together with Phellodendron bark (making the sum of them to be 600-1,200 g).

In the extraction process above, Phellodendron bark, *Scutellaria baicalensis, Paeonia lactiflora* and *Mentha arvensis* may be used. In such an extraction process, the Phellodendron bark extract is in an amount of 15-60% by weight, the *Scutellaria baicalensis* extract is in an amount of 3-30% by weight, the *Paeonia lactiflora* extract is in an amount of 12-50% by weight and the *Mentha arvensis* extract is in an amount of 5-25% by weight.

The lower limit of the total amount of the plants used in the extraction above may be 600 g, 610 g, 620 g, 630 g, 640 g, 650 g, 660 g, 670 g, 680 g, 690 g, 700 g, 710 g, 720 g, 730 g, 740 g, 750 g, 760 g, 770 g, 780 g, 790 g, 800 g, 810 g, 820 g, 830 g, 840 g, 850 g, 860 g, 870 g, 880 g, 890 g, 900 g, 950 g, 1000 g, 1050 g, 1100 g or 1150 g. The upper limit of the total amount of the plants used in the extraction above may be 610 g, 620 g, 630 g, 640 g, 650 g, 660 g, 670 g, 680 g, 690 g, 700 g, 710 g, 720 g, 730 g, 740 g, 750 g, 760 g, 770 g, 780 g, 790 g, 800 g, 810 g, 820 g, 830 g, 840 g, 850 g, 860 g, 870 g, 880 g, 890 g, 900 g, 950 g, 1000 g, 1050 g, 1100 g, 1150 g or 1200 g.

Further, the present disclosure provides a topical skin or hair product comprising the composition and a dermatologically acceptable carrier. The product may comprise the composition in an amount of 0.01% to 99.9% by weight.

The lower limit above may be 1% by weight, 2% by weight, 3% by weight, 4% by weight, 5% by weight, 6% by weight, 7% by weight, 8% by weight, 9% by weight, 10% by weight, 20% by weight, 30% by weight, 40% by weight, 50% by weight, 60% by weight, 70% by weight, 80% by weight, 90% by weight, 91% by weight, 92% by weight, 93% by weight, 94% by weight, 95% by weight, 96% by weight, 97% by weight, 98% by weight, 98.5% by weight and 99% by weight.

The upper limit above may be 99% by weight, 98.5% by weight, 98% by weight, 97% by weight, 96% by weight, 95% by weight, 94% by weight, 93% by weight, 92% by weight, 91% by weight, 90% by weight, 80% by weight, 70% by weight, 60% by weight, 50% by weight, 40% by weight, 30% by weight, 20% by weight, 10% by weight, 9% by weight, 8% by weight, 7% by weight, 6% by weight, 5% by weight, 4% by weight, 3% by weight, 2% by weight and 1% by weight.

The composition, the topical skin or hair product may further comprise one of more of 2-Bromo-2-Nitropropane-1,3-Diol, 4-Hydroxybenzoic Acid, 5-Bromo-5-Nitro-1,3-Dioxane, Dehydroacetic Acid, Dimethyl Oxazolidine, Diazolidinyl Urea, DMDM Hydantoin, Dichlorobenzyl Alcohol, Lauralkonium Chloride, Laurtrimonium Bromide, Laurtrimonium Chloride, Magnesium Salicylate, Methylisothiazolinone, Methylparaben, Benzalkonium Chloride, Benzoic Acid, Benzyl Alcohol, Butylparaben, Bromochlorophene, Cetrimonium Bromide, Cetrimonium Chloride, Sodium Dehydroacetate, Sodium Methylparaben, Sodium Benzoate, Sodium Borate, Sodium Salicylate, Sodium Formate, Sodium Propylparaben, Sodium o-Phenylphenate, Sorbic Acid, Iodopropynyl Butylcarbamate, Ethylparaben, Ethyl Lauroyl Arginate HCl, Undecylenic Acid, Imidazolidinyl Urea, Isobutylparaben, Isopropylparaben, Zinc Undecylenate, Zinc Pyrithione, Calcium Propionate, Quatemium-15, Chlorobutanol, Chloroxylenol, Chlorphenesin, Chlorhexidine Digluconate, Climbazole, Triclosan, Triclocarban, Triclocarban, Phenoxyethanol, Phenoxyisopropanol, Phenyl Salicylate, Formaldehyde, Potassium Benzoate, Potassium Sorbate, Polyaminopropyl Biguanide, Propionic Acid, Propylparaben, Piroctone Olamine, Hexamidine Diisethionate, o-Cymen-5-ol, 1,2-hexanediol, Zanthoxylum Piperitum Fruit Extract, pulsatilla Koreana Extract, Usnea Barbata (Lichen) Extract and Citrus Paradisi (Grapefruit) Fruit Extract.

The skin care product comprises a facial spray, a body spray, a facial mask, a cream, a skin cleanser, a moisturizer, a lotion, a skin softener, a foundation, a night cream, a toner, a sunscreen, a facial mask, etc. and a body-care product such as body cleanser, a body cream, a body lotion.

In another embodiment, there is a provided a hair-care product such as a shampoo, a conditioner, a treatment, or a hair spray.

These products may take the form of topically spreadable formulations, sprayable formulations, and aerosolized formulations.

These products may take the form of washable or leave-on formulations.

Further, the present disclosure provides cosmetics comprising the present composition for improving atopy. The cosmetics for improving atopy comprise a mist, a spray, a cream, tissues and baby hygiene products such as baby wipes, baby bath liquid or soap and baby shampoo.

In addition, the present disclosure provides products comprising the present composition for improving skin conditions caused by pressure or friction on the skin such as pressure sore or decubitus ulcer. Such products comprise a mist, a spray, a cream, a mask pack, an ointment and a patch.

Further, the present disclosure provides products comprising the present composition for improving skin conditions caused by heat such as heat rash and blisters.

Moreover, the present disclosure provides products comprising the present composition for improving sunburn.

In addition, the present disclosure provides products comprising the present composition for cooling skin after treatments such as brow lift, eyelid lift (blepharoplasty), ear pinning surgery, otoplasty, face grafting, neck lift, breast reduction, breast lift, breast implant revision, breast reconstruction, arm lift, tummy tuck, mini tummy tuck, liposuction, thigh lift, lipo-abdominoplasty, scar revision, etc. Such products comprise a mist, a spray, a cream, a mask pack, an ointment and a patch.

Furthermore, the present disclosure provides products comprising the present composition for improving skin conditions such as itching, acne, eczema, pimple, HFMD (hand, foot and mouth disease), psoriasis, flushing and tinea pedis. Such products comprise a mist, a spray, a cream, a mask pack, an ointment and a patch.

In addition, the present disclosure provides deodorants comprising the present composition.

Moreover, the present disclosure provides scalp care products comprising the present composition. Such products comprise a mist, a spray, a cream, a mask pack, an ointment and a patch.

Further, the present disclosure provides products comprising the present composition for improving hair loss or alopecia. Such products comprise a mist, a spray, a cream, a mask pack, an ointment and a patch.

Further, the present disclosure provides a method of cooling skin comprising applying a composition, comprising a Phellodendron bark extract as a main ingredient, to a skin of a subject, wherein the skin needs cooling.

In the method of cooling skin, the composition may further comprise an extract of *Anemarrhena asphodeloides*.

In the method of cooling skin, the composition may further comprise an extract of one or more selected from the group consisting of *Anemarrhena asphodeloides, Scutellaria baicalensis*, and *Paeonia lactiflora, Dictamnus dasycarpus, Alumen, Dryobalanops aromatic, Mentha arvensis, Inula helenium, Lonicera japonica, Eclipta prostrata* and *Glycyrrhiza uralensis* FISCH.

In the method of cooling skin, the composition may further comprise an extract of *Anemarrhena asphodeloides*,

*Scutellaria baicalensis, Paeonia lactiflora, Dictamnus dasycarpus, Alumen, Dryobalanops aromatic* and *Mentha arvensis*.

In the method of cooling skin, the composition may further comprise an extract of *Anemarrhena asphodeloides, Scutellaria baicalensis, Paeonia lactiflora, Dictamnus dasycarpus, Alumen, Dryobalanops aromatic, Mentha arvensis, Inula helenium, Lonicera japonica, Eclipta prostrata* and *Glycyrrhiza uralensis* FISCH.

In the method of cooling skin, the composition may comprise a Phellodendron bark extract in an amount of 30-80% by weight and an *Anemarrhena asphodeloides* extract in an amount of 20-70% by weight.

In the method of cooling skin, the composition may comprise an extract of Phellodendron bark and *Anemarrhena asphodeloides* in an amount of 35-50% by weight and an extract of *Scutellaria baicalensis, Paeonia lactiflora, Dictamnus dasycarpus, Alumen, Dryobalanops aromatic* and *Mentha arvensis* in an amount of 50-65% by weight.

In the method of cooling skin, the composition may comprise an extract of Phellodendron bark, *Scutellaria baicalensis, Paeonia lactiflora* and *Mentha arvensis*. In such a composition, the Phellodendron bark extract is in an amount of 15-60% by weight, the *Scutellaria baicalensis* extract is in an amount of 3-30% by weight, the *Paeonia lactiflora* extract is in an amount of 12-50% by weight and the *Mentha arvensis* extract is in an amount of 5-25% by weight.

In the method of cooling skin, the skin comprises face skin, scrotum skin, scalp, arm fit, and any skin area which needs cooling. A skin area which needs cooling may include, but not limited to, skin surface which is injured by burn, cut, infection, etc.

In addition, the present disclosure provides a composition for cooling skin comprising one or more plant extracts wherein the plant is selected from the group consisting of Phellodendron bark, *Anemarrhena asphodeloides, Scutellaria baicalensis, Paeonia lactiflora, Dictamnus dasycarpus, Alumen, Dryobalanops aromatic Mentha arvensis, Inula helenium, Lonicera japonica, Eclipta prostrata* and *Glycyrrhiza uralensis* FISCH.

Further, the present disclosure provides a method of preparing a composition for cooling skin comprising one or more plant extracts wherein the plant is selected from the group consisting of Phellodendron bark, *Anemarrhena asphodeloides, Scutellaria baicalensis, Paeonia lactiflora, Dictamnus dasycarpus, Alumen, Dryobalanops aromatic, Mentha arvensis, Inula helenium, Lonicera japonica, Eclipta prostrata* and *Glycyrrhiza uralensis* FISCH as follows. 600-1,200 g of one or more plant(s) selected from the group consisting of Phellodendron bark, *Anemarrhena asphodeloides, Scutellaria baicalensis, Paeonia lactiflora, Dictamnus dasycarpus, Alumen, Dryobalanops aromatic, Mentha arvensis, Inula helenium, Lonicera japonica, Eclipta prostrata* and *Glycyrrhiza uralensis* FISCH, are washed with purified water, and then put in a super fast low temperature vacuum extractor which contains a liquid phase extractor and a gas phase distillation part, together with 15-25 L of a first solvent, and a vacuum extraction is performed for 50-80 minutes at 60-80° C. to obtain a distillation solution in the gas phase distillation part and a liquid extract in the liquid phase extractor, and optionally the first solvent is removed from the liquid extract to obtain a concentrated extract. Such a distillation solution or a concentrated extract may be used as a plant extract which could be used in preparing a composition for cooling skin. The first solvent is one or more selected from the group consisting of alcohol, glycols, oils, water and purified water.

Further, the present disclosure provides a method of preparing a composition for cooling skin comprising one or more plant extracts wherein the plant is selected from the group consisting of Phellodendron bark, *Anemarrhena asphodeloides, Scutellaria baicalensis, Paeonia lactiflora, Dictamnus dasycarpus, Alumen, Dryobalanops aromatic* and *Mentha arvensis* as follows. 600-1,200 g of one or more plant(s) selected from the group consisting of Phellodendron bark, *Anemarrhena asphodeloides, Scutellaria baicalensis, Paeonia lactiflora, Dictamnus dasycarpus, Dryobalanops aromatic, Mentha arvensis, Inula helenium, Lonicera japonica, Eclipta prostrata* and *Glycyrrhiza uralensis* FISCH, are washed with purified water, and then put in a super fast low temperature vacuum extractor which contains a liquid phase extractor and a gas phase distillation part, together with 15-25 L of a first solvent, and a vacuum extraction is performed for 50-80 minutes at 60-80° C. to obtain a distillation solution in the gas phase distillation part and a liquid extract in the liquid phase extractor, and optionally, the first solvent is removed from the liquid extract to obtain a concentrated extract. In addition, 80-130 g of *Alumen* are added to 3-10 L of a second solvent and warm impregnation is performed at 65-80° C. for 50-80 minutes and filtered, and then a filtrate is mixed with the distillation solution in a ratio of 5:1 to 1:1 (the distillation solution: the filtrate) to prepare a stock solution. The ratio between the distillation solution and the filtrate may be 4.5:1, 4:1, 3.5:1, 3:1, 2.5:1, 2:1 or 1.5:1. The first solvent is one or more selected from the group consisting of alcohol, glycols, oils, water and purified water. The second solvent is one or more selected from the group consisting of alcohol, glycols, oils, water and purified water.

Further, the present disclosure provides a skin care product comprising a composition comprising one or more plant extracts wherein the plant is selected from the group consisting of Phellodendron bark, *Anemarrhena asphodeloides, Scutellaria baicalensis, Paeonia lactiflora, Dictamnus dasycarpus, Alumen, Dryobalanops*. The skin care product comprises a facial spray, a body spray, a facial mask, a cream, a mist, a patch, etc.

Further, the present disclosure provides a method of cooling skin comprising applying a composition, comprising one or more plant extracts wherein the plant is selected from the group consisting of Phellodendron bark, *Anemarrhena asphodeloides, Scutellaria baicalensis, Paeonia lactiflora, Dictamnus dasycarpus, Alumen, Dryobalanops aromatic Mentha arvensis, Inula helenium, Lonicera japonica, Eclipta prostrata* and *Glycyrrhiza uralensis* FISCH, to a skin of a subject in need thereof.

According to the present disclosure, when a composition including Phellodendron bark is applied on the skin of a human body, the composition exhibits effects of preventing a burning sensation in the skin and under the skin and reducing heat generated under the skin and on the skin. In particular, the composition has an effect of removing skin fever and keeping the skin cool in physically vulnerable environments such as a sitting posture, compression, use of a disposable diaper.

To enhance the efficacy thereof, the composition may further comprises an extract of one or more selected from the group consisting of *Anemarrhena asphodeloides, Scutellaria baicalensis, Paeonia lactiflora, Dictamnus dasycarpus, Alumen, Dryobalanops aromatic*, and *Mentha arvensis*, thereby exhibiting effects of preventing and treating itching, eczema, odor, furuncle, rash, etc.

Further, the composition is used to prepare skin-cooling and skin-improving products by including such a composition for cooling the skin as well as the testicles of men and baby boys in the form of a functional spray, an ointment, a gel, a cream, a powder, a patch pad, etc., these products being easy to use.

The plant which is used to obtain the plant extract included in a composition for cooling skin may comprise one or more extract of Phellodendron bark, *Anemarrhena asphodeloides, Scutellaria baicalensis, Paeonia lactiflora, Dictamnus dasycarpus, Alumen, Dryobalanops aromatic* and *Mentha arvensis, Inula helenium, Lonicera japonica, Eclipta prostrata* and *Glycyrrhiza uralensis* FISCH. The plant extract may be obtained by subjecting the group of plants which can be selected from the above to the extraction process all together. Alternatively, each of plant may be subjected to the extraction process and such plant extracts obtained therefrom may be mixed later.

DESCRIPTION OF THE DRAWINGS

FIG. 4 is a photo showing the location of the body where thermometers were attached in Experimental Example 2.

DESCRIPTION OF EMBODIMENTS

Figure 1:
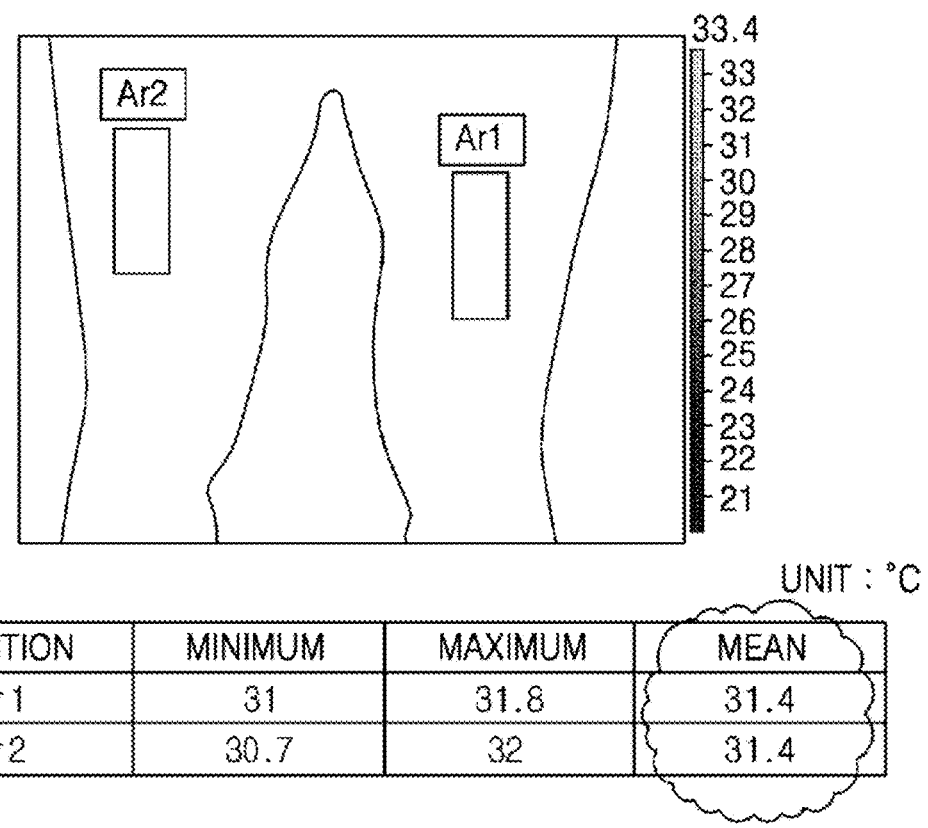
FIGS. 1 and 2 illustrate the conditions before and after the attachment of a patch pad (Ar1) comprising a concentrated extract of a composition for cooling skin according to the present disclosure, and a patch pad (Ar2) comprising a distillation solution of the composition, respectively.

Hereinafter, specific embodiments of the present disclosure will be described in more detail.

The present disclosure relates to a composition for cooling skin by using a Phellodendron bark extract including Phellodendron bark as a main ingredient, which is developed to prevent a burning sensation in the skin and under the skin and to reduce heat generated under the skin and on the skin, a method of preparing the same, a skin-improving product using the same and a method of cooling skin by applying the same to a skin of a subject in need thereof.

Phellodendron bark, which may be a main component of the composition, is dried bark of Phellodendron amurense belonging to the family Rutaceae. The bark is stripped from the trunk of a tree to remove coarse bark or the bark is cut, and then dried in the sun to be used as a drug. According to Korean Traditional Herbal Medicine Volumes including the Korean Pharmacopeia, Phellodendron bark has a bitter flavor and is cold in nature, and has efficacies of dissipating heat away and eliminating dampness, detoxicating, and eliminating fever caused by blood deficiency, and has a bactericidal activity against *E. coli*, typhoid, and cholera bacteria and a strong antibacterial activity against Gram-positive bacteria and gonococcus.

Further, berberine, a component of Phellodendron bark, has a strong local astringent action, and thus is used externally for itching, and also has efficacies of removing heat toxins of wounds or burns. As such, when the Phellodendron bark having the local astringent cooling action, the antimicrobial activity, the anti-inflammatory effect, and the effects of eliminating dampness and stopping itching is used as a main ingredient in the composition, a burning sensation in the skin and under the skin may be prevented and heat generated under the skin and on the skin may be reduced.

Further, the Phellodendron bark is a natural medicine which has a bitter taste, is used as a drug for strengthening the digesting functions of the stomach, stopping diarrhea, and controlling the intestinal function, and has efficacies of reducing fever, detoxifying, soothing pain, etc.

The objects of the present disclosure may be achieved by using only Phellodendron bark having the above efficacies. However, to enhance the effects, the Phellodendron bark may be used as a main ingredient, and one or more herbal medicines selected from the group consisting of *Anemarrhena asphodeloides, Scutellaria baicalensis, Paeonia lactiflora, Dictamnus dasycarpus, Alumen, Dryobalanops aromatic*, and *Mentha arvensis* may be further included in the combination, and all these herbal medicines may be included to prepare a composition.

With regard to the efficacies of the above components, first, *Anemarrhena asphodeloides* has efficacies of cooling heat and dissipating heat away, and nourishing body fluid and moistening dryness, and in particular, *Anemarrhena asphodeloides* includes a large amount of ingredients that make the skin firm and elastic. Therefore, when it is used together with Phellodendron bark, their effects are strengthened by each other and thus efficacy thereof is maximized. It is preferable that *Anemarrhena asphodeloides* is primarily used together with Phellodendron bark.

Further, *Anemarrhena asphodeloides* is used for reducing fever, quenching thirst, and treating symptoms of chest tightness and restless movements of the legs and arms, and has therapeutic effects on cough and dry cough, ache in the joints, fever that occurs like the high tide and low tide, and cold sweat by promoting production of body fluids.

*Scutellaria baicalensis* has efficacies of cooling heat and drying dampness, eliminating heat and toxins, and stopping bleeding by cooling blood, and thus is used for endothelial injury, anticonvulsant, antifungal, and antimicrobial actions by making it into medicine by boiling.

Further, *Scutellaria baicalensis* reduces excessive heat to improve symptoms of high body fever, severe chest and limb discomfort and thirst, and indistinct consciousness in severe cases, and exhibits a high antipyretic effect from high fever caused by cold to high fever caused by general infectious diseases. *Scutellaria baicalensis* removes ocular irritation and pain caused by excessive heat accumulated in the body, is used for hypertension, headache, nosebleed, and uterine bleeding, and also shows its efficacy on skin irritation and boils. Such efficacies are attributed to its cold nature, which reduces fever to relieve the symptoms. When *Scutellaria baicalensis* is taken during pregnancy, diseases occurring during pregnancy may be treated. Further, *Scutellaria baicalensis* quenches thirst caused by high fever, and relieves fever and pain in the joints of the whole body, and exhibits anti-inflammatory and anti-pathogenic actions, antipyretic, diuretic, and hypotensive actions, hypoglycemic and hypolipidaemic actions, and choleretic and sedative actions.

*Paeonia lactiflora* has efficacies of cooling heat and cooling blood, removing blood stagnation and stopping a pain, and thus is used for disease symptoms such as ocular irritation, tumentia, furuncle, etc.

*Dictamnus dasycarpus* has efficacies of reducing heat and detoxicating, and eliminating dampness and stopping itching, and thus is used for disease symptoms such as furuncle, itching, jaundice, etc.

*Alumen* has an astringent action and has efficacies of drying dampness and stopping itching to remove discomfort and odor in the site of inflammation, and is used as an astringent agent for skin mucosal inflammation or used as a local astringent agent for rinsing oral cavity.

*Dryobalanops aromatic* has efficacies of opening the sensory organs, clearing the mind, reducing fever, and removing pain, and thus shows sedative, analgesic, and preservative actions, and is used for the treatment of burns, eczema, and infectious corneitis and used to soften the skin.

*Mentha arvensis* has efficacies of dispelling epidemic pathogenic factor of wind-heat, and cooling head and eyes, and functions to dilate capillaries of the skin and to promote secretion of sweat glands to remove heat, and therefore, it is used for the purpose of reducing fever and stopping itching.

These medicines are natural medicines, and non-toxic to the human body when used externally, and a blend thereof, an extract stock solution thereof, or a distillation solution thereof may reduce heat under the skin and on the skin, and remove itching, odor while giving topical sensation of refreshment, and exhibit antimicrobial and sedative effects.

In particular, to reduce heat in the testicles of men and baby boys and to obtain additional efficacies, the composition is extracted in the form of a high pressure boiled liquid extract, a distillation solution, a powder, etc., and mixed with a pharmaceutically acceptable carrier, and then prepared in the form of a powder, a gel, a liquid mixture, a high pressure boiled liquid extract, etc., which is used to prepare skin-cooling and skin-improving products such as a functional spray, an ointment, a gel, a cream, a powder, a patch pad, etc.

When the composition is prepared in the form of a liquid, it is preferable that the composition is directly sprayed or applied onto the testicles or the skin, or onto underwear or a diaper that is in direct contact with the testicles in an amount of about 0.2-0.4 cc per application. When the composition is a powder, the composition is directly sprayed onto the testicles or the skin, or evenly applied onto underwear or diaper in an amount of about 0.5-1.0 g per application. In this case, the composition is preferably used as a wetting dressing by sweat, feces and urine, etc. It is preferable that when the composition is a gel, it is directly applied to the skin uniformly. The composition is an extract obtained by high pressure boiling of natural herbal medicines, and it is non-toxic to the human body and has no side-effects in use.

When the above-described composition of the present disclosure is prepared by using only Phellodendron bark and *Anemarrhena asphodeloides*, the composition may include 30-80% by weight of Phellodendron bark and 20-70% by weight of *Anemarrhena asphodeloides*.

When the composition is prepared by using all of Phellodendron bark, *Anemarrhena asphodeloides, Scutellaria baicalensis, Paeonia lactiflora, Dictamnus dasycarpus, Alumen, Dryobalanops aromatic,* and *Mentha arvensis,* the composition may preferably include 35-50% by weight of Phellodendron bark and *Anemarrhena asphodeloides* and 50-65% by weight of the other ingredients, *Scutellaria baicalensis, Paeonia lactiflora, Dictamnus dasycarpus, Alumen, Dryobalanops aromatic,* and *Mentha arvensis.*

Further, the composition is prepared by using all of Phellodendron bark, *Anemarrhena asphodeloides, Scutellaria baicalensis, Paeonia lactiflora, Dictamnus dasycarpus, Alumen, Dryobalanops aromatic,* and *Mentha arvensis,* the composition may preferably include 15-35% by weight of Phellodendron bark, 10-23% by weight of *Anemarrhena asphodeloides,* 3-15% by weight of *Scutellaria baicalensis,* 12-25% by weight of *Paeonia lactiflora,* 7-15% by weight of *Dictamnus dasycarpus,* 12-25% by weight of *Alumen,* 0.7-5% by weight of *Dryobalanops aromatic,* and 1-7% by weight of *Mentha arvensis.*

These composition ratios of the herbal medicines are obtained, based on the prescriptions of Korean Traditional Herbal Medicine Volumes and experimental results regarding the maximization and persistence of reducible temperature.

Mode of the Invention

The present invention will be described in more detail with reference to the following Examples and Experimental Examples. However, the present invention is not limited to these examples, and these Examples are not intended to limit the scope of the present invention.

The following Examples, Experimental Examples and Preparation Examples relate to the preparation of a natural herb liquid extract capable of preventing a burning sensation in the skin and under the skin and reducing heat generated under the skin and on the skin.

Conditions of the following Examples include washing 600-1,200 g of one or more plant(s) selected from the group consisting of Phellodendron bark, *Anemarrhena asphodeloides, Scutellaria baicalensis, Paeonia lactiflora, Dictamnus dasycarpus, Alumen, Dryobalanops aromatic* and *Mentha arvensis* with purified water, and then putting the washed plant in a super fast low temperature vacuum extractor which contains a liquid phase extractor and a gas phase distillation part, together with 15-25 L of purified water, and performing low temperature vacuum extraction for 50-80 minutes at 60-80° C. to obtain a distillation solution in the gas phase distillation part and a liquid extract in the liquid phase extractor, and purified water is removed from the liquid extract to obtain a concentrated extract. Herein, 80-130 g of *Alumen* were added to 3-10 L of purified water and warm impregnation was performed at 65-80° C. for 50-80 minutes and filtered, and then a filtrate was mixed with the composition in a ratio of 2:1 to prepare a stock solution.

Example 1

1,000 g of Phellodendron bark was washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

Example 2

600 g of Phellodendron bark and 400 g of *Anemarrhena asphodeloides* were washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

Example 3

500 g of Phellodendron bark, 100 g of *Scutellaria baicalensis*, and 400 g of *Anemarrhena asphodeloides* were washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

Example 4

300 g of Phellodendron bark, 200 g of *Dictamnus dasycarpus*, and 200 g of *Anemarrhena asphodeloides* were washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

Example 5

300 g of Phellodendron bark, 200 g of *Paeonia lactiflora*, and 200 g of *Anemarrhena asphodeloides* were washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

Example 6

300 g of Phellodendron bark, 200 g of *Dictamnus dasycarpus*, 200 g of *Paeonia lactiflora*, and 100 g of *Anemarrhena asphodeloides* were washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

Example 7

300 g of Phellodendron bark, 50 g of *Scutellaria baicalensis*, 150 g of *Dictamnus dasycarpus*, 150 g of *Paeonia lactiflora*, 100 g of *Anemarrhena asphodeloides*, 10 g of *Mentha arvensis*, and 20 g of *Dryobalanops aromatic* were washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

Example 8

300 g of Phellodendron bark, 50 g of *Scutellaria baicalensis*, 150 g of *Dictamnus dasycarpus*, 150 g of *Paeonia lactiflora*, 100 g of *Anemarrhena asphodeloides*, 10 g of *Mentha arvensis*, and 20 g of *Dryobalanops aromatic* were washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

Then, 100 g of *Alumen* was added to 5 L of purified water and warm impregnation was performed at 65-80° C. for 1 hour and filtered, and then a filtrate was mixed with the distillation solution in a ratio of 2:1 (the distillation solution: the filtrate) to prepare a stock solution.

Example 9

300 g of Phellodendron bark, 50 g of *Alumen*, 50 g of *Scutellaria baicalensis*, 150 g of *Dictamnus dasycarpus*, 150 g of *Paeonia lactiflora*, 100 g of *Anemarrhena asphodeloides*, 10 g of *Mentha arvensis*, and 20 g of *Dryobalanops aromatic* were washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

Example 10

300 g of Phellodendron bark, 50 g of *Alumen*, 30 g of *Inula helenium*, 50 g of *Scutellaria baicalensis*, 150 g of *Dictamnus dasycarpus*, 150 g of *Paeonia lactiflora*, 100 g of *Anemarrhena asphodeloides*, 10 g of *Mentha arvensis*, and 20 g of *Dryobalanops aromatic* were washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

Example 11

300 g of Phellodendron bark, 50 g of *Alumen*, 30 g of *Inula helenium*, 50 g of *Lonicera japonica*, 50 g of *Scutel-* laria baicalensis, 150 g of *Dictamnus dasycarpus*, 150 g of *Paeonia lactiflora*, 100 g of *Anemarrhena asphodeloides*, 10 g of *Mentha arvensis*, and 20 g of *Dryobalanops aromatic* were washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

Example 12

300 g of Phellodendron bark, 50 g of *Alumen*, 30 g of *Inula helenium*, 50 g of *Lonicera japonica*, 100 g of *Eclipta prostrata*, 50 g of *Scutellaria baicalensis*, 150 g of *Dictamnus dasycarpus*, 150 g of *Paeonia lactiflora*, 100 g of *Anemarrhena asphodeloides*, 10 g of *Mentha arvensis*, and 20 g of *Dryobalanops aromatic* were washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

Example 13

300 g of Phellodendron bark, 60 g of *Scutellaria baicalensis*, 150 g of *Paeonia lactiflora*, 10 g of *Mentha arvensis* were washed with purified water, and then put in a super fast low temperature vacuum extractor which contains a liquid phase extractor and a gas phase distillation part, together with 20 L of purified water, and low temperature vacuum extraction was performed for 1 hour at 60-80° C. to obtain 10 L of a distillation solution in the gas phase distillation part and a liquid extract in the liquid phase extractor, and the purified water is removed from the liquid extract to obtain 5 L of a concentrated extract.

In Examples 1-13, *Glycyrrhiza uralensis* FISCH may be further added in an amount of 3-15% by weight in the plants before washing with purified water.

(Experimental Example 1) Test of Patch Pads Comprising the Concentrated Extract or the Distillation Solution Obtained in Example 7

Figure 2:
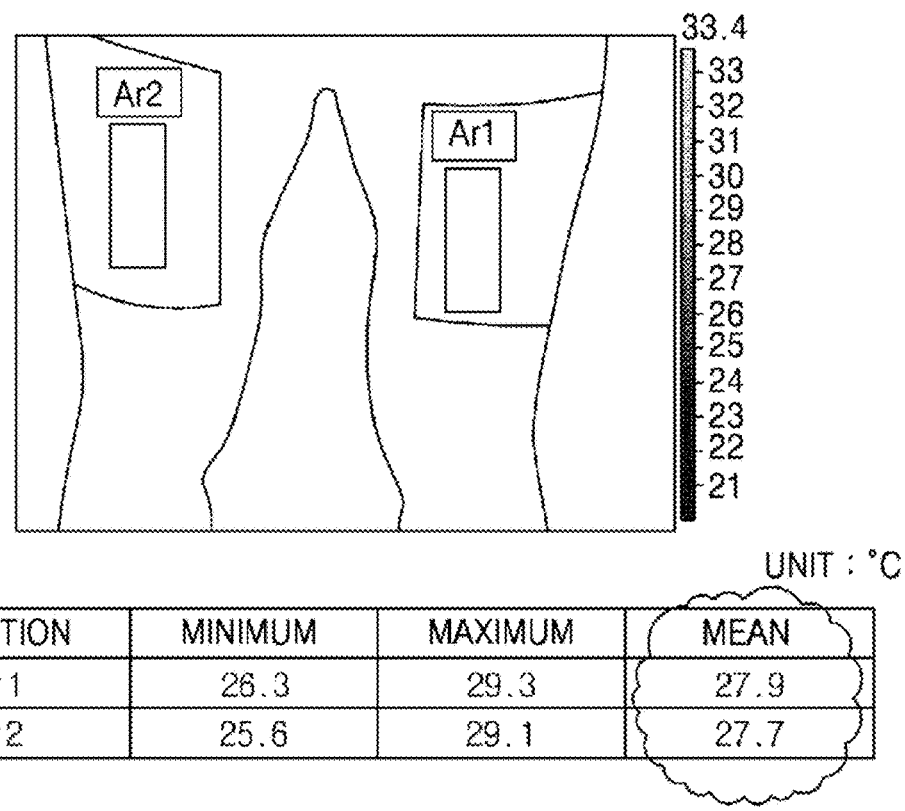
Figure 3:
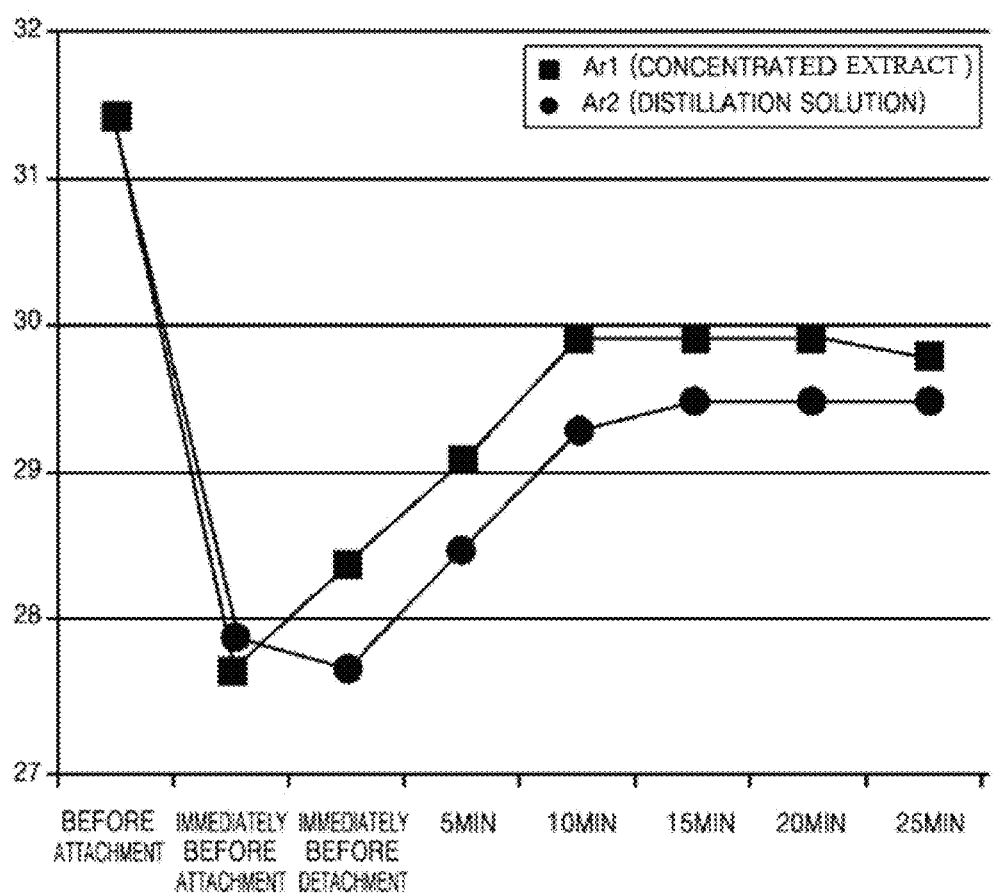
FIG. 3 is a graph showing the experimental results of FIGS. 1 and 2.

The experimental results regarding patch pads comprising the concentrated extract or the distillation solution obtained in Example 7 are illustrated in FIGS. 1 to 3.

Ar1 is a patch pad comprising the concentrated extract obtained in Example 7, Ar2 is a patch pad comprising the distillation solution obtained in Example 7, and FIGS. 1 and 2 illustrate the conditions before and after attachment of the patch pads, respectively, and FIG. 3 is a graph showing the results.

The experimental results are as follows.
1) All, 31.4° C., before attachment of the patch pads;
2) Ar1—27.7° C., Ar2—28.4° C. upon detachment at 10 minutes after attachment of the patch pads; and
3) Ar1—29.5° C., Ar2—29.8° C. upon detachment at 25 minutes after attachment of the patch pads.

Referring to the above experimental results, when the patch pad (Ar1), to which the concentrated extract of the above natural material including Phellodendron bark of the present invention was applied, was attached on the skin of which temperature was 31.4° C. before attachment, the temperature decreased to about 27.9° C. immediately after attachment, and 10 minutes later, the temperature further decreased to about 27.7° C. Then, when the patch pad was detached, the temperature of the skin gradually increased over time, but the temperature between 10-25 minutes after detachment was maintained at about 29.5° C., as shown in the graph of the experimental data.

When the patch pad (Ar2), to which the distillation solution was applied, was attached on the skin of which temperature was 31.4° C. before attachment, the temperature decreased to about 27.7° C. immediately after attachment. The temperature of the skin gradually increased over time after attachment of the patch pad, and 10 minutes later, the temperature increased to about 28.4° C. Even after detachment of the patch pad, the temperature rise was maintained over time. However, the temperature between 10-25 minutes after detachment was maintained at about 29.8° C., as shown in the application test of the concentrated extract.

(Experimental Example 2) Test of a Spray Solution Comprising the Distillation Solution Obtained in Example 9

A spray solution comprising the distillation solution obtained in Example 9 was used in this Experimental Example.

A thermometer was attached at a lower side of testis of each of Test Persons A and B as shown in FIG. 4 and Test Persons A and B have worn underwear and pants and stayed for 30 minutes. Then, Test persons A and B took off pants and underwear, and the spray solution was sprayed on the lower side of testis of each of Test Persons A and B that the thermometer is attached. Then, Test Persons A and B have worn underwear and pants again and stayed for 90 minutes.

Figure 5:
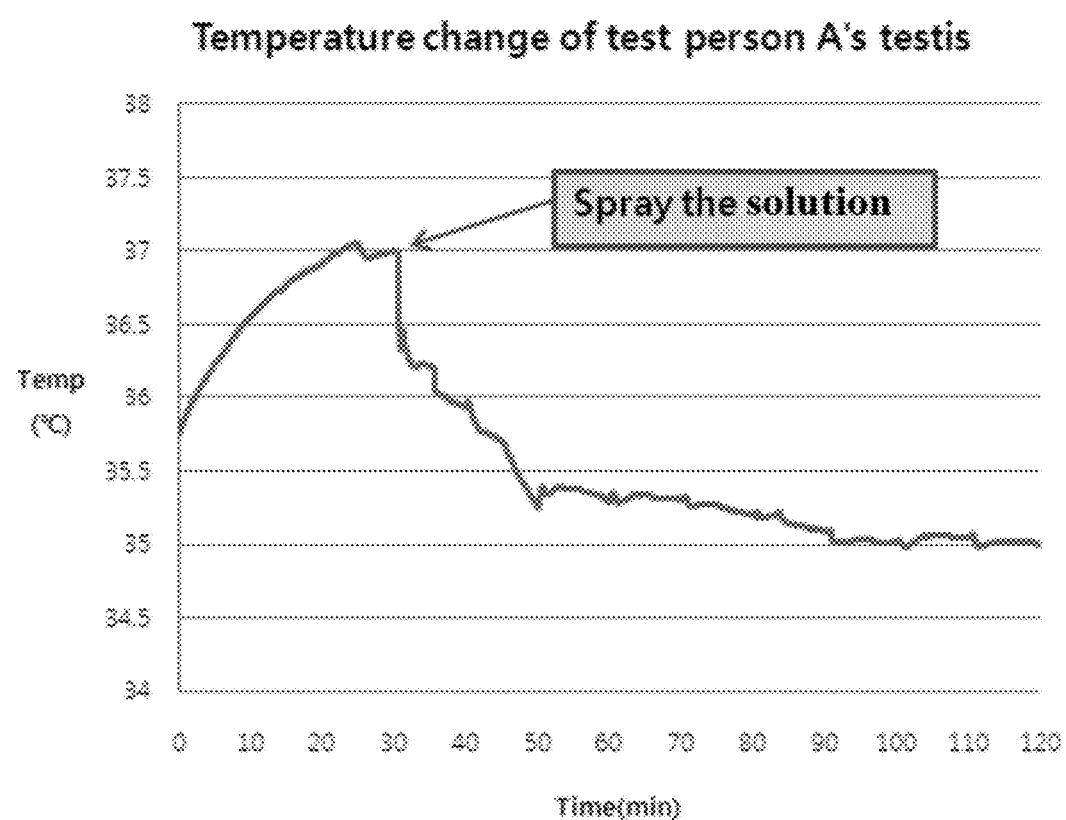
FIG. 5 is a graph showing the temperature change of Test Person A's testis.

The temperature of the testis of Test Person A measured during 120 minutes is shown in Table 1 and FIG. 5.

TABLE 1

| Start | 10 min | 20 min | 30 min | 31 min | 35 min | 40 min | 50 min |
|---|---|---|---|---|---|---|---|
| 35.76° C. | 36.56° C. | 36.93° C. | 37.01° C. | 36.42° C. | 36.22° C. | 35.94° C. | 35.26° C. |
| 60 min | 70 min | 80 min | 90 min | 100 min | 110 min | 120 min | |
| 35.29° C. | 35.31° C. | 35.21° C. | 35.09° C. | 35.02° C. | 35.05° C. | 35.00° C. | |

Figure 6:
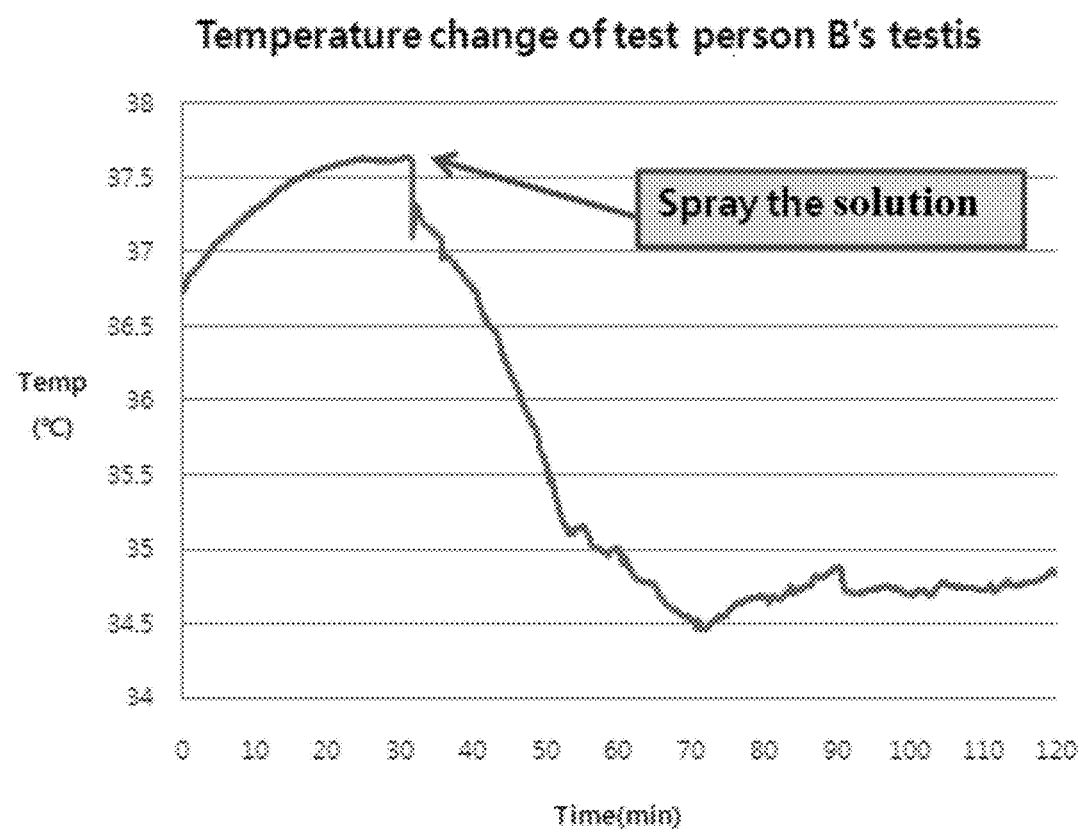
FIG. 6 is a graph showing the temperature change of Test Person B's testis.

The temperature of the testis of Test Person B measured during 120 minutes is shown in Table 2 and FIG. 6.

TABLE 2

| Start | 10 min | 20 min | 30 min | 31 min | 35 min | 40 min | 50 min |
|---|---|---|---|---|---|---|---|
| 36.73° C. | 37.28° C. | 37.57° C. | 37.63° C. | 37.25° C. | 37.12° C. | 36.76° C. | 35.58° C. |
| 60 min | 70 min | 80 min | 90 min | 100 min | 110 min | 120 min | |
| 35.00° C. | 34.52° C. | 34.68° C. | 34.88° C. | 34.70° C. | 34.73° C. | 34.83° C. | |

As shown in Tables 1 and 2 and FIG. 6, in both Test Persons A and B, the temperature of the testis has increased gradually while wearing underwear and pants (0 to 30 minutes), but the temperature of the testis has quickly decreased after spraying the solution (30 minutes) and the temperature around 35° C. has been maintained for two hours.

From the results above, it was confirmed that the composition according to this disclosure is effective in cooling the temperature of the testis while wearing underwear and pants and such an effect lasts for a long period.

(Experimental Example 3) Comparison Test Between Water and the Distillation Solution Obtained in Example 12

A spray solution comprising the distillation solution obtained in Example 12 was used in this Experimental Example and its cooling effect was compared with that of water.

Figure 7:
FIG. 7 is a photo showing the location of the body where the temperature was measured in Experimental Example 3.

The spray solution was sprayed on the right arm at the location shown in FIG. 7 and water was sprayed on the left arm at the location shown in FIG. 7 and Test Persons A, B and C participated in the experiment.

Figure 8A:
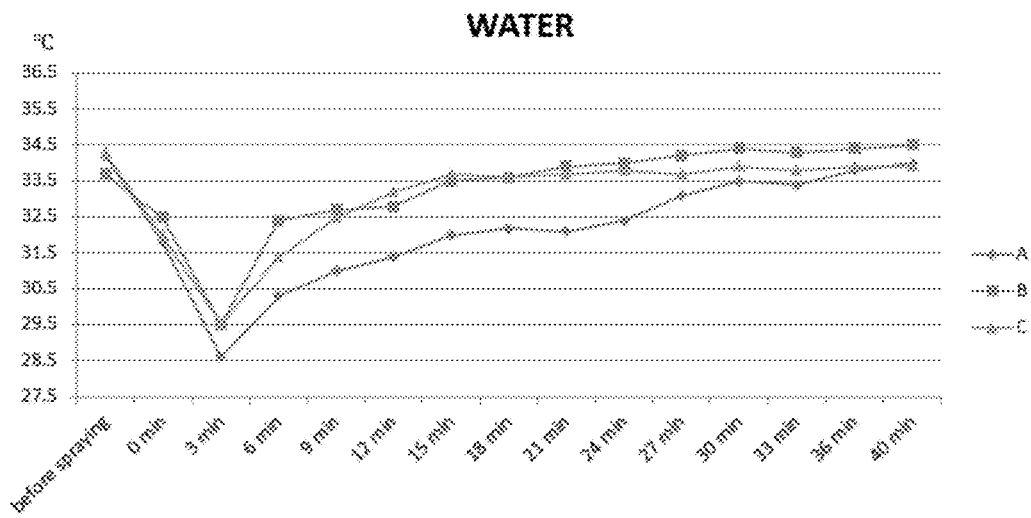
FIG. 8*a* is a graph showing the temperature change where water was sprayed in Experimental Example 3.
Figure 8B:
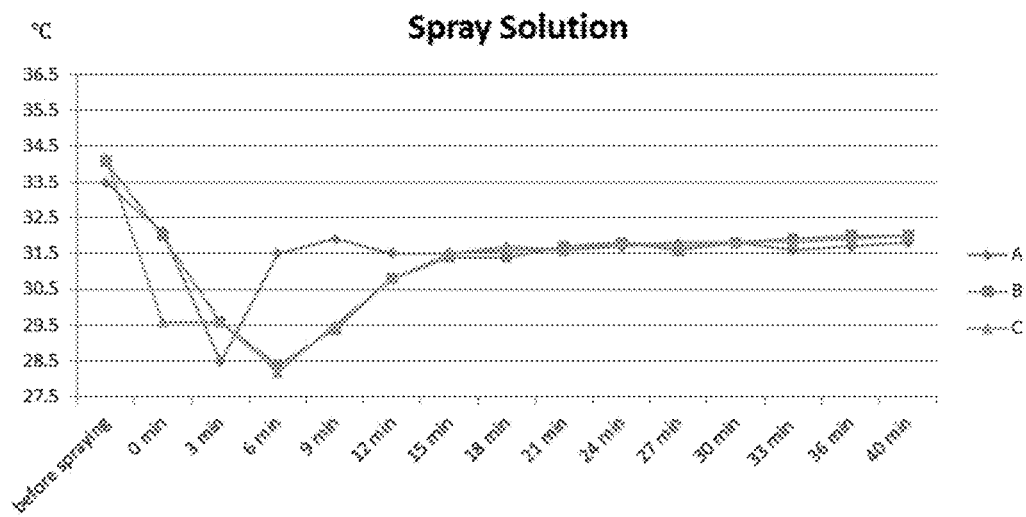
FIG. 8*b* is a graph showing the temperature change where the spray solution was sprayed in Experimental Example 3.

The Temperature of the arms of each Test Person was measured right before the spraying and until 40 minutes after the spraying and is shown in Table 3 and FIG. 8a (water) and FIG. 8b (spray solution).

TABLE 3

| | Before spraying | 0 | 3 | 6 | 9 | 12 | 15 | 18 | 21 | 24 | 27 | 30 | 33 | 36 | 40 |
|---|---|---|---|---|---|---|---|---|---|---|---|---|---|---|---|
| | | | | | | | Water | | | | | | | | |
| A | 34.2 | 31.8 | 28.6 | 30.3 | 31 | 31.4 | 32 | 32.2 | 32.1 | 32.4 | 33.1 | 33.5 | 33.4 | 33.8 | 34 |
| B | 33.7 | 32.5 | 29.5 | 32.4 | 32.7 | 32.8 | 33.5 | 33.6 | 33.9 | 34 | 34.2 | 34.4 | 34.3 | 34.4 | 34.5 |
| C | 34.3 | 32 | 29.5 | 31.4 | 32.5 | 33.2 | 33.7 | 33.6 | 33.7 | 33.8 | 33.7 | 33.9 | 33.8 | 33.9 | 33.9 |
| | | | | | | | Spray solution | | | | | | | | |
| A | 33.5 | 32.1 | 28.5 | 31.5 | 31.9 | 31.5 | 31.5 | 31.6 | 31.6 | 31.7 | 31.8 | 31.8 | 31.6 | 31.7 | 31.8 |
| B | 34.1 | 32 | 29.6 | 28.4 | 29.4 | 30.8 | 31.4 | 31.4 | 34.7 | 31.8 | 31.6 | 31.8 | 31.9 | 32 | 32 |
| C | 34.2 | 29.6 | 29.6 | 28.2 | 29.5 | 30.8 | 31.5 | 31.7 | 31.6 | 31.8 | 31.7 | 31.8 | 31.8 | 31.9 | 32 |

As shown in Table 3 and FIG. 8a and FIG. 8b, after spraying water, the temperature has decreased temporarily but quickly increased again to the similar temperature with the temperature before spraying. However, after spraying the spray solution, the temperature has decreased and then increased as time goes by, but maintained the lower temperature than the temperature before spraying.

From the results above, it was confirmed that the composition according to this disclosure is effective in cooling the skin temperature.

(Preparation Example 1) Hydrogel Soothing Mask

A hydrogel soothing mask was prepared including the following ingredients.

Water, Dipropylene Glycol, Glycerin, Phellodendron Amurense Bark Extract, Niacinamide, *Paeonia Lactiflora* Bark/Sap Extract, *Scutellaria Baicalensis* Root Extract, Caprylic/Capric Triglyceride, Ceratonia Siliqua Gum, 1,2-Hexanediol, Chondrus Crispus Powder, *Mentha Arvensis* Extract, Cetyl Ethylhexanoate, Butylene Glycol, Glyceryl Stearate, *Paeonia Suffruticosa* Root Extract, Centella Asiatica Extract, Cellulose Gum, Sodium Polyacrylate, Allantoin, Chamomilla Recutita (Matricaria) Flower Extract, Hydrogenated Polydecene, Glyceryl Caprylate, Polysorbate 20, Rehmannia Glutinosa Root Extract, Adenosine, Ethylhexylglycerin, Honey Extract, Trideceth-6, *Glycyrrhiza Glabra* (Licorice) Root Extract, Sesamum Indicum (Sesame) Seed Extract, Sophora Flavescens Root Extract, Angelica Gigas Root Extract, Cimicifuga Racemosa Root Extract, Poria Cocos Extract, Morus Alba Bark Extract, Phellinus Linteus Extract, Rosa Multiflora Fruit Extract, Artemisia Princeps Leaf Extract, Panax Ginseng Root Extract, *Paeonia Albiflora* Root Extract, Hovenia Dulcis Fruit Extract, Polygonum Multiflorum Root Extract, Disodium EDTA, Fragrance (Preparation Example 2) Lifting Mask A lifting mask was prepared including the following ingredients.

Water, Butylene Glycol, Glycerin, Phellodendron Amurense Bark Extract, *Paeonia Lactiflora* Bark/Sap Extract, *Scutellaria Baicalensis* Root Extract, Glycereth-26, 1,2-Hexanediol, *Mentha Arvensis* Extract, Glyceryl Acrylate/Acrylic Acid Copolymer, PVM/MA Copolymer, Sodium Hyaluronate, PEG/PPG-17/6 Copolymer, Hydroxyacetophenone, Acrylates/C10-30 Alkyl Acrylate Crosspolymer, Cellulose Gum, Adenosine, Allantoin, Dipotassium Glycyrrhizate, Betaine, Polysorbate 80, Menthyl PCA, Ethyl Menthane Carboxamide, Tocopheryl Acetate, Tromethamine, Caprylyl Glycol, Ethylhexylglycerin, Disodium EDTA, Fragrance.

(Preparation Example 3) All in One Cream

An all in one cream was prepared including the ingredients as follows.

Phellodendron Amurense Bark Extract, *Paeonia Lactiflora* Bark/Sap Extract, *Dictamnus Dasycarpus* Root Extract, *Anemarrhena Asphodeloides* Root Extract, *Eclipta Prostrata* Extract, *Scutellaria Baicalensis* Root Extract, *Mentha Arvensis* Extract, *Inula Helenium* Extract, Cinnamomum Camphora (Camphor) Leaf Extract, 1,2-Hexandiol), Glycerin, Cyclopentasiloxane, PEG-30 Dipolyhydroxystearate, Glycereth-26, Macadamia Integrifolia Seed Oil, Cetearyl Glucoside, Pentaerythrityl Tetraethylhexanoate, Phytosqualane, Methyl Gluceth-20, Niacinamide, Cetyl Ethylhexanoate, Cetearyl Alcohol, Caprylic/Capric Triglyceride, Argania Spinsosa Kernel Oil, Methyl Glucose Sesquistearate, Glyceryl Stearate, PEG-100 stearate, Cetearyl Olivate, Sorbitan Olivate, Stearic acid, Butyrospermum oarkii (Shea Butter), Ammonium Acryloydimethyltaurate/ VP Copolymer, Xanthan Gum, Caprylhydroxamic Acid, Caprylyl Glycol, Tocopheryl Acetate, Fragrance, Adenosine.

(Preparation Example 4) UV Protection Cream

An UV protection cream was prepared including the following ingredients. Phellodendron Amurense Bark Extract, *Paeonia Lactiflora* Bark/Sap Extract, Ethylhexyl Methoxycinnamate, *Dictamnus Desycarpus* Root EXTRACT, Cyclopentasiloxane, Dicaprylyl Carbonate, Octocrylene, Caprylic/Capric Triglyceride, Glycyrhiza Glabra (Licorice) Root Extract, *Anemarrhena Asphodeloides* Root Extract, *Eclipta Prostrata* Extract, 1,2-Hexanediol, *Scutellaria Baicalensis* Root Extract, *Inula Helenium* Extract, *Mentha Arvensis* Extract, Dimethicone, Cetyl PEG/PPG-10/1 Dimethicone, Plantago Asiatica Extract, *Lonicera Japonica* (Honeysuckle) Flower Extract, Niacinamide, Butyl Methoxydibenzoylmethane, Glycerin, Butylene Glycol, Cinnamomum Camphora (Camphor) Leaf Extract, Titanium dioxide, Bis-Ethylhexyloxyphenol methoxyphenyl Triazine, Methylene Bis-Benzotriazolyl Tetramethylbutylphenol, Sodium Chloride, Adenosine, Tocopheryl Acetate, Centella Asiatica Extract, Menthol, Madecassoside, Sodium Hyaluronate, Sorbitan Olivate, Glyceryl Bhehenate/Eicosadioate, Cetyl Dimethicone, Stearalkonium Hectorite, Ceresin, Dimethicone/Vinyl Dimethicone Crosspolymer, Propylene Carbonate, Xanthan Gum, Polymethyl Methacrylate, Polyhydroxystearic Acid, Dimethicone/PEG-10/15 Crosspolymer, Fragrance, Disodidum EDTA.

(Preparation Example 5) Mist

A mist was prepared including the following ingredients. Water, Phellodendron Amurense Bark Extract, *Paeonia Lactiflora* Bark Extract, *Dictamnus Desycarpus* Root Extract, Alumimum Sulfate, *Anemarrhena Asphodeloides* Root Extract, *Eclipta Prostrata* Extract, *Glycyrrhiza Glabra* (Licorice) Root Extract, *Scutellaria Baicalensis* Root Extract, *Mentha Arvensis* Extract, *Inula Helenium* Extract, *Lonicera Japonica* (Honeysuckle) Flower Extract, Plantago Asiatica Extract, Cinnamomum Camphora (Camphor) Leaf Extract, Butylene Glycol, Fragrance.

Taken together, the present disclosure demonstrates that the composition functions to prevent a burning sensation in the skin and under the skin and to reduce heat generated under the skin and on the skin.

What is claimed is:

1. A method of preparing a plant extract comprising:
   (a) washing a plant with water, wherein the plant is Phellodendron bark; and
   (b) putting the washed plant and a first solvent at a volume ratio of 1:12 to 1:42 in a vacuum extractor which contains a liquid phase extractor and a gas phase distillation part, and performing a vacuum extraction for 50-80 minutes at 60-80° C. to obtain a distillation solution in the gas phase distillation part and a liquid extract in the liquid phase extractor; and
   (c) optionally, removing the first solvent from the liquid extract to obtain a concentrated extract,
   wherein the distillation solution in (b) or the concentrated extract in (c) is the plant extract.

2. The method according to claim 1 further comprising:
   (d) adding *Alumen* to a second solvent in a volume ratio of 1:23 to 1:334 and performing a warm impregnation at 65-80° C. for 50-80 minutes and filtering to obtain a filtrate; and
   (e) mixing the filtrate of (c) with the distillation solution of (b) in a volume ratio of 5:1 to 1:1 (the distillation solution of (b): the filtrate of (d)) to prepare a stock solution,
   wherein the stock solution is the plant extract.

3. The method according to claim 1, wherein the first solvent is one or more selected from the group consisting of alcohol, glycols, oils and water.

4. The method according to claim 2, wherein the second solvent is one or more selected from the group consisting of alcohol, glycols, oils and water.

5. The method according to claim 1, wherein the plant of (a) further comprises one or more selected from the group consisting of *Anemarrhena asphodeloides, Scutellaria baicalensis, Paeonia lactiflora, Dictamnus dasycarpus, Alumen, Dryobalanops aromatic* and *Mentha arvensis*.

6. The method according to claim 1, wherein the plant of (a) further comprises *Anemarrhena asphodeloides, Scutellaria baicalensis, Paeonia lactiflora, Dictamnus dasycarpus, Alumen, Dryobalanops aromatic* and *Mentha arvensis*.

* * * * *